United States Patent [19]

Wachob et al.

[11] Patent Number: 4,810,471

[45] Date of Patent: Mar. 7, 1989

[54] VACUUM MANIFOLD FOR EXTRACTION PROCESSING

[75] Inventors: George D. Wachob, State College; Robert W. Rightnour, Mingoville, both of Pa.

[73] Assignee: Rohm and Haas Co., Philadelphia, Pa.

[21] Appl. No.: 890,013

[22] Filed: Jul. 24, 1986

[51] Int. Cl.$^4$ .............................................. G01N 1/18
[52] U.S. Cl. .................................... 422/103; 422/101; 422/59; 422/70; 436/178; 436/161; 141/8; 141/65; 141/243; 222/553; 222/555; 251/84; 251/88
[58] Field of Search ................... 422/103, 101, 69, 70, 422/58, 59; 436/177, 178, 161; 222/553, 555; 141/8, 65, 242, 243; 251/84, 88

[56] References Cited

U.S. PATENT DOCUMENTS

| | | | |
|---|---|---|---|
| 3,225,972 | 12/1965 | Brumbach | 222/55 |
| 4,055,202 | 10/1977 | Greene | 141/59 |
| 4,079,009 | 3/1978 | Seiler et al. | 210/198.2 |
| 4,231,989 | 11/1980 | Thoma | 422/103 X |
| 4,461,328 | 7/1984 | Kenney | 73/864.02 X |

*Primary Examiner*—Barry S. Richman
*Assistant Examiner*—Lynn M. Kummert

[57] ABSTRACT

A vacuum manifold for solid phase extraction of a plurality of liquid samples from reagent tubes removably connected by valves to a vacuum chamber through a removable vacuum tight cover closing. A plurality of parallel flow paths are provided through the cover for the flow of liquid samples into the vacuum chamber, through a plurality of valves rotatable about an axis parallel to the general direction of flow through the cover to provide flow adjustment and closing of the valves. A valve is also provided for attaching the vacuum chamber to a vacuum source to create a vacuum therein. An optional attachment is provided permitting treatment of materials with nitrogen or other gases using a manifold plate attached to a source of gas and providing a plurality of valve control means axially aligned to couple with the rotatable valves for passage of liquid into the vacuum chamber.

14 Claims, 5 Drawing Sheets

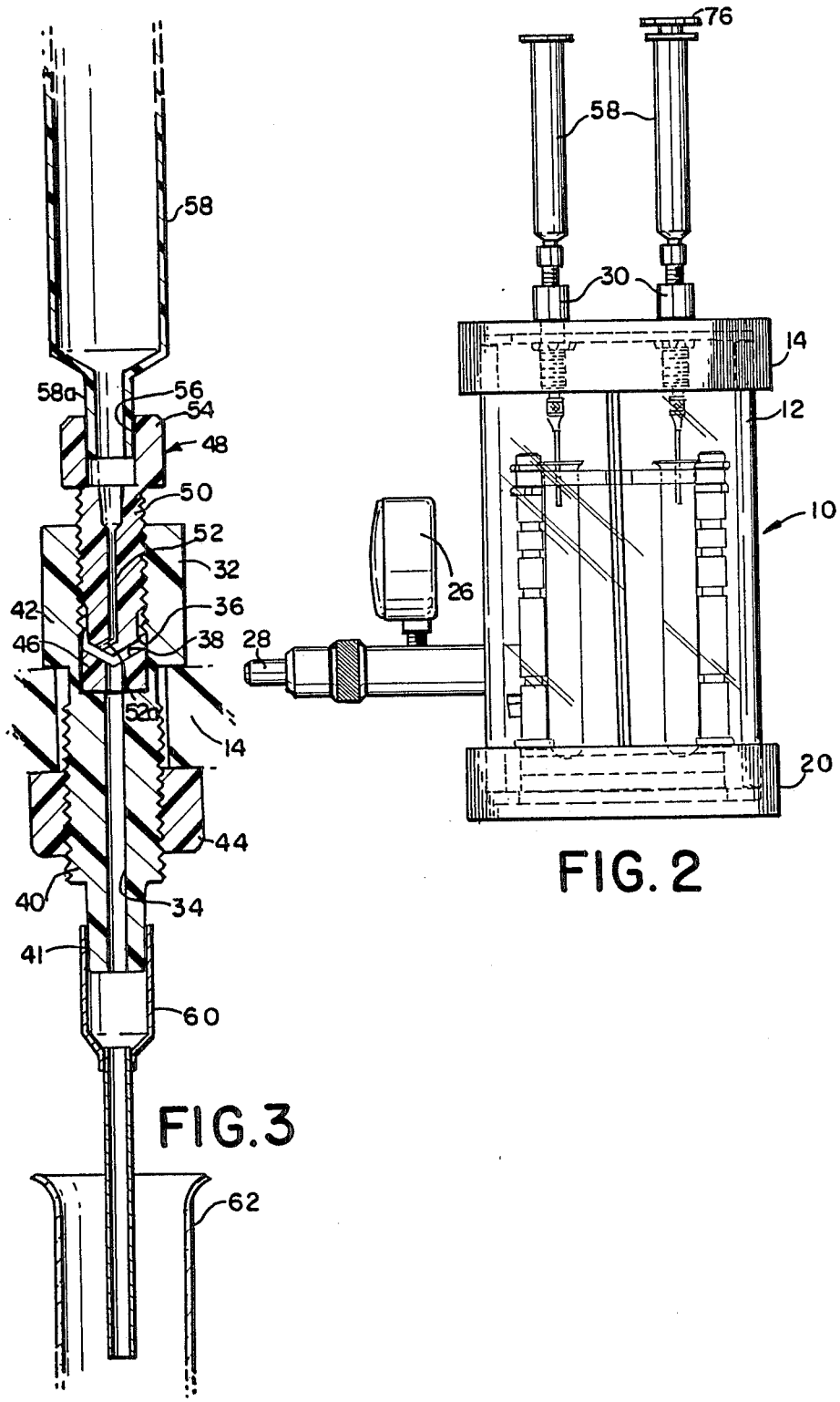

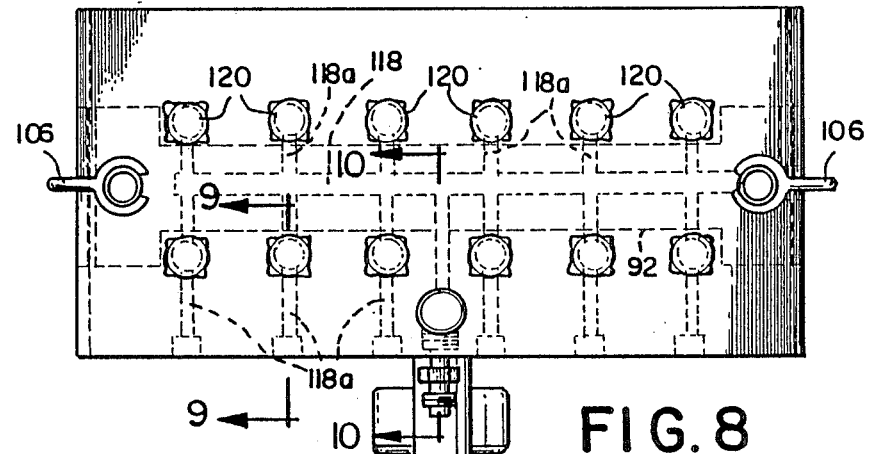
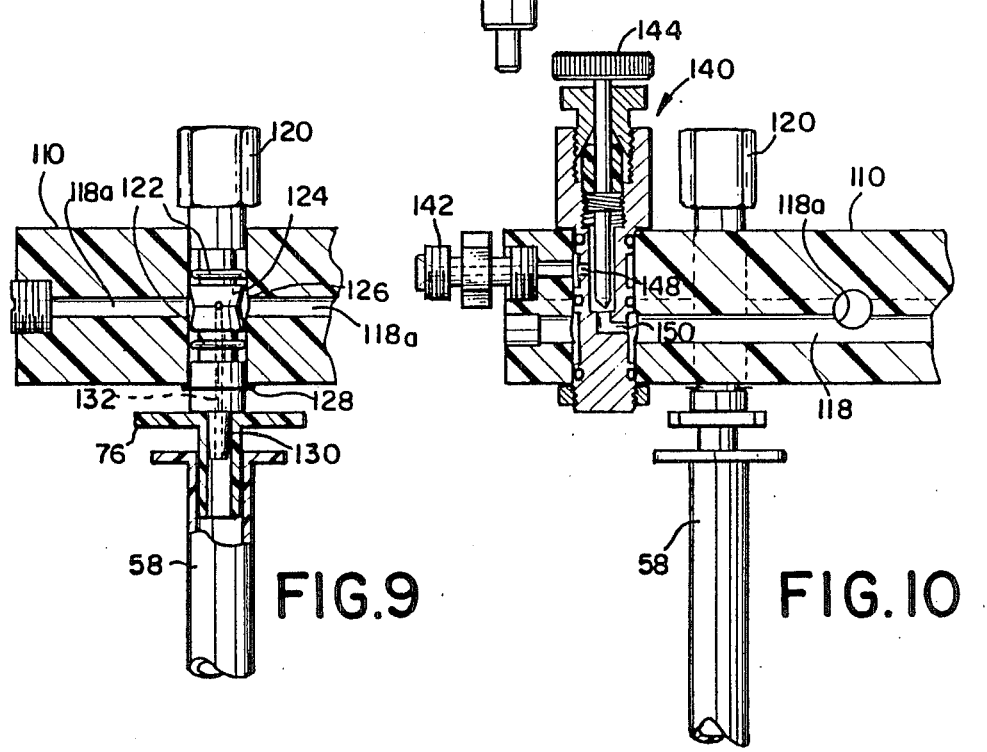
FIG. 8
FIG. 9
FIG. 10

VACUUM MANIFOLD FOR EXTRACTION PROCESSING

FIELD OF THE INVENTION

The invention relates to the field of sample preparation and, in particular, to a vacuum manifold device useful for obtaining or preparing chromatography samples by solid phase extraction. The vacuum manifold device lends itself particularly to running a plurality of liquid samples in parallel for the purpose of testing for, or removing, the same or different constituents in samples. A further aspect of the invention provides for an attachment permitting introduction of nitrogen or other gases into the manifold.

BACKGROUND AND PRIOR ART

Preparation and treatment of liquid samples by solid phase extraction is a known process whereby liquid samples are cleaned by removing targeted substances from the samples prior to chromatographic analysis. Generally, the process involves eluting the liquid samples through a solid adsorptive packing material, which solid packing usually consists of a silica-based material in bead or powder form. The elution may be more readily accomplished under the influence of a vacuum which draws the liquid samples through the solid packing material. In this manner, targeted contaminants or substances may be selectively removed from the liquid samples.

It is known in the art to construct a manifold device capable of eluting multiple liquid samples through solid packing material simultaneously. In a prior art device of this type, a vacuum chamber is provided whereby the vacuum acts to simultaneously elute a plurality (i.e., more than one) of samples. The vacuum chamber, which in the prior art has generally been constructed of either stainless steel or an opaque plastic material, is provided with a plurality of fittings in the lid or cover. The fittings may be used directly to support and drain a reagent tube, or may have had interposed in the flow path a stopcock-controlled valve. The reagent tubes consist of packed columns containing said silica material, and having a leuer connection to be placed into each of the valve fittings and supported thereby on the lid of the vacuum chamber. Liquid samples poured into the reagent tubes pass through the packed columns and are drawn through the silica material by the vacuum force into the vacuum manifold. Test tubes or other collection vessels are provided in the vacuum chamber to collect the eluent from each of the valves.

Transparent material, such as clear plastic, has been used for the housing for the vacuum chamber, so that the operator can observe the collection of eluent in the test tubes inside the chamber to monitor the progress of the sample preparation.

To the extent that vacuum manifolds known in the prior art have been provided with control valves, they have been difficult to use because they have relied on conventional stopcocks. In particular, when a plurality of reagent tubes are in place on the manifold, stopcocks have proved to be a cumbersome means of regulating the flow of the liquid samples. During a multiple extraction process, stopcock-type valves may be difficult to reach and provide an awkward means of manipulation.

SUMMARY OF THE INVENTION

The invention is directed to an improved vacuum manifold structure for processing chromatography samples by solid phase extraction. A vacuum manifold made in accordance with the invention includes coaxial, screw-type valve means which are easy to regulate and which provide precise and gradual control of the flow of the liquid samples. In particular, the valving means controlling the rate of sample elution comprises in-line valves having a rotatable, regulating valve member which coaxially accommodates reagent tubes containing solid packing material. The in-line valves control flow by coaxial rotation of the rotatable valve members supporting the coaxial reagent tubes. Adjustment of the flow rate of sample elution is readily accomplished by simply rotating the reagent tube itself which is frictionally engaged in the rotating member of the valve. Each reagent tube adjusts the corresponding coaxial valve from fully closed to fully open position, or from fully open to fully closed position, simply by coaxial rotation of the reagent tube by the operator. In this manner, a minimum of operator attention must be devoted to adjustment of the valves since a convenient structure is provided for precisely regulating each valve in such a way as to create a minimum of interference by other tubes and valves. The in-line valve structure provides both minimum obstruction and maximum manual control surface.

A vacuum manifold made in accordance with the invention is useful in performing multiple extractions or other processing of materials sought to be analyzed by chromatography. The manifold device includes a vacuum chamber which is provided with a removable cover providing both access to the manifold and sealing of the vacuum chamber. Means providing a plurality of generally parallel flow paths extend through the cover of the vacuum chamber. Said flow path means include said in-line valve means for closing off and regulating the flow of eluent in each flow path. Rotation of a rotatable valve member in a plane generally normal to the overall flow path permits flow adjustment and closing of the valve means. Preferably the rotatable valve member is provided with an inner bore for receiving, frictionally engaging and coaxially supporting reagent tubes or the like containing solid absorbent. The valve means permits valve opening or closing by rotating the valve itself or the reagent tube supported thereby. Means is also provided for attaching a vacuum source to the vacuum chamber to draw samples from the reagent tubes into the vacuum chamber.

In preferred embodiments of the invention, the vacuum chamber is formed of glass, or at least provided with a glass window for viewing the progress of the process within the vacuum chamber. The use of glass lends itself to easy cleaning, and the transparency of the vacuum chamber is not altered by age or exposure to staining or corrosive substances. It will be understood by those skilled in the art that, from a functional standpoint, the shape and relative dimensions of the vacuum chamber, as well as the varying types of materials from which the vacuum chamber may be constructed, is a matter of choice. The applicant, however, has provided a pleasing design for the combination of the chamber and its cover, which is preferred for aesthetic reasons but forms no part of the functioning of the present invention. The design is covered by copending United States design patent application Ser. No. 857,801, filed April 28, 1986 now U.S. Pat. No. Des. 289,861, issued May 19, 1987.

In a further aspect of the invention, a nitrogen purge device is provided for clearing the system with a gas, such as nitrogen. The purge device is operable in conjunction with the vacuum manifold device disclosed herein to dry collected eluent in the collection means in the vacuum chamber, to dry the solid packing, or to increase the rate of elution.

DECRIPTION OF THE DRAWINGS

For a better understanding of the invention, reference is made to the accompanying drawings in which:

FIG. 2 is a side elevational view of a vacuum manifold apparatus made in accordance with the invention;

FIG. 3 is an enlarged sectional view taken along line 3—3 of FIG. 1;

FIG. 8 is a top plan view of a nitrogen purge device made in accordance with the invention affixed onto a vacuum manifold device made in accordance with the invention;

FIG. 9 is an enlarged sectional view taken along line 9—9 in FIG. 8; and

FIG. 10 is an enlarged sectional view taken along line 10—10 in FIG. 8.

DETAILED DESCRIPTION OF THE INVENTION

The vacuum manifold device and nitrogen purge device made in accordance with the invention are useful for solid phase extraction to clean or prepare chromatography samples. The liquid sample can be, for example, an aqueous sample or a biological sample. As an example of an aqueous solution, a solution of an organic chemical in water may be extracted to remove the chemical from the eluent. A biological sample may be treated to remove, for example, vitamins, proteins and drugs.

Figure 1:
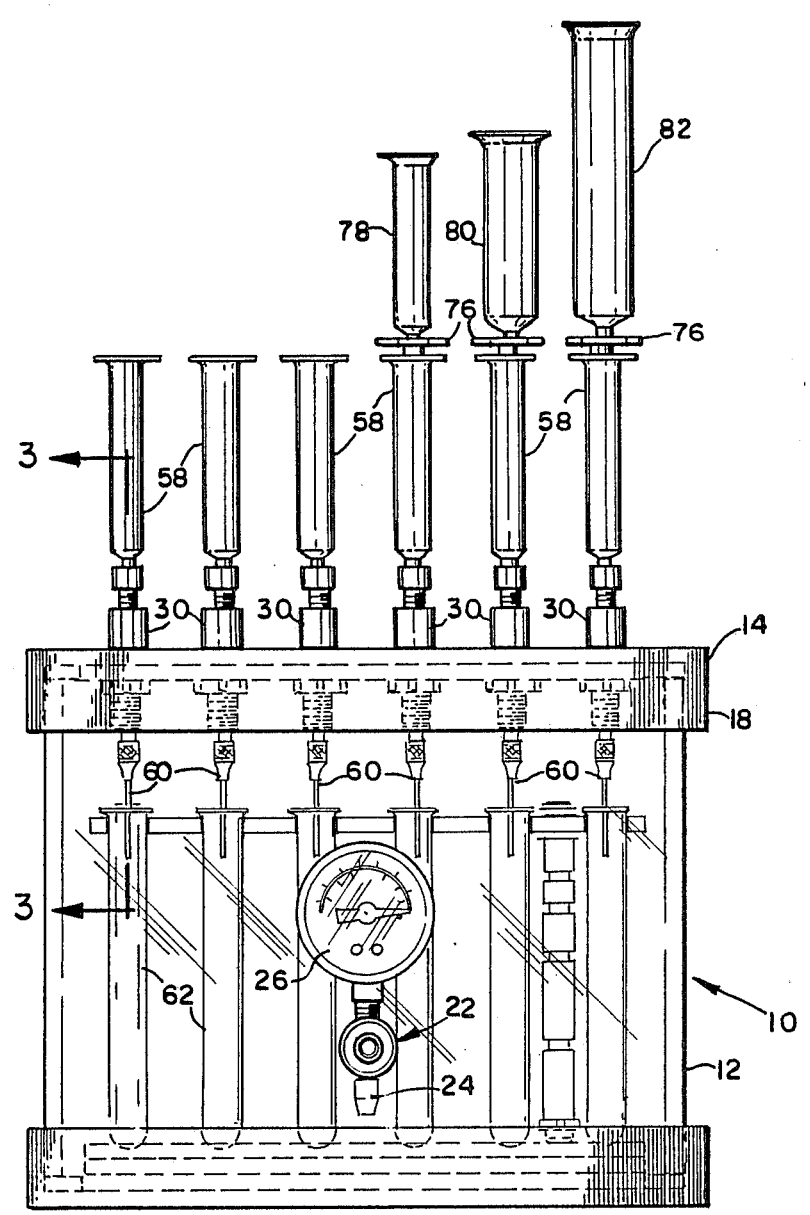
FIG. 1 is a front elevational view of a vacuum manifold apparatus made in accordance with the invention fitted with reagent tubes of varying size.

Referring now to FIG. 1, a vacuum manifold device is designated generally at 10. The manifold device is provided with a vacuum chamber 12 consisting of a closed vacuum tight container. In the preferred embodiment of the invention, a glass building block, from which the top has been removed, forms enclosure 12 of general rectangular form having four walls and a bottom. It will be understood that the particular shape or appearance of the vacuum chamber 12 is immaterial. Use of a glass brick as the vacuum chamber 12 is wholly arbitrary from a functional standpoint, but is preferred as a matter of design appearance, a factor in the applicant's copending design patent application Ser. No. 857,801 now U.S. Pat. No. Des. 289,861, issued May 19, 1987. A glass container of any other size, shape, wall thickness, or design features is functionally satisfactory and is intended to be within the scope of the invention. However, use of glass of whatever shape or form is desirable because it allows the operator to monitor, inside the chamber, the progress of the extraction process. Also, glass is durable, and may be easily cleaned and is not damaged in the event that the glass is exposed to chemicals. The invention, however, contemplates use of a chamber which is only partly glass as well, for example, if a glass window were placed in the wall of the chamber.

The vacuum chamber is provided with a conforming access portion or removable cover 14. Cover 14 includes a sealing element 16 (FIG. 4) preferably contained in a channel which overlies the top edge of the vacuum chamber 12. The sealing element forms a vacuum tight seal between the vacuum chamber and cover 14. The cover may be of whatever size and shape is needed in a particular embodiment to close and seal the vacuum chamber and may have various design features such as an extended skirt or surface design, as desired. In the preferred embodiment, cover 14 is formed of a durable plastic material, such as polypropylene, while the sealing element 16 is formed of a more resilient material, such as foamed polyethylene. Around its entire periphery, cover 14 has uniform sidewalls 18 which snugly embrace the vacuum chamber 12. The manifold is also provided with a removable base portion 20 having a flat base and uniform sidewalls which enclose the base of the chamber. The base 20 is of the same general shape and external appearance as the cover 14. The vacuum chamber 12 may be placed in the base portion 20 for stability during use. The base portion 20 is also preferably formed of a hard plastic material such as polypropylene. It is noted that the plastic for the base and top, like the glass materials forming the chamber, are selected, in part, on the basis of their solvent resistance.

A vacuum valve 22 extends through one wall, preferably the front wall, as shown, of the vacuum chamber 12 and is suitably sealed to hold it in position. The vacuum valve 22 may also be provided with a solvent siphon nozzle 24 within the vacuum chamber 12 to draw off liquids which may accumulate in the bottom of the chamber. On the exterior side of the vacuum chamber, the vacuum valve is provided with a gauge 26 to register the vacuum or reduced air pressure within the vacuum chamber. Also provided is a fitting 28 (FIG. 2) which is connectable ultimately to a vacuum pump (not shown) to produce a vacuum in the vacuum chamber 12.

Extending through the cover 14 into the vacuum chamber 12 are a plurality of valve means, designated generally as 30 in FIG. 1, for providing individual supports for multiple reagent tubes 58. Reagent tubes 58 contain a suitable adsorptive material. The valve means 30 further provide flow paths into the vacuum chamber 12 from the reagent tubes 58. The configuration of each of the valve means 30 can be more clearly viewed in FIG. 3. As seen in FIG. 3, the valve means extend both above and below the cover 14. Each of the valve means 30 comprises a stationary valve member 32 and a rotating valve member 48. Stationary valve member 32 is secured to the cover 14. Stationary valve member 32 is also formed preferably of a plastic or resinous material similar to the material of the cover 14. As seen in FIG. 3, stationary valve member 32 consists of three sections of decreasing diameter, labeled 42, 40, and 41, respectively, providing flat radial shoulders between them normal to the axis. The intermediate diameter portion 40 of each valve preferably passes snugly through a conforming hole in the cover 14 and is provided with a radial planar shoulder between the intermediate diameter portion 40 and the large diameter portion 42 to rest and seal against the top of cover 14.

Stationary valve member 32 is firmly secured and sealed to cover 14 with securing nut 44, which is threaded to engage the threaded outer surface of intermediate diameter portion 40, one of the parallel radial faces of securing nut 44 engaging the bottom of cover 14.

Each stationary valve member 32 is provided along its length with an axial center bore 34 which is counterbored of its larger diameter end to provide a large diameter bore 36 which is internally threaded. The shoulder between the two bore diameters is preferably radially directed in a plane normal to the axis of the bore. Together axial center bores 34 and 36 form a passage through the entire stationary valve member 32 and form a flow path through cover 14.

Positioned internally within stationary valve member 32 is a seat 46, which is preferably formed of Teflon ®. Seat 46 has a diameter corresponding to large diameter portion 42 and is supported internally of the bore on the shoulder between large diameter bore 36 and smaller bore 34. As shown, seat 46 has a central bore of the same diameter as axial center bore 34. Seat 46 is provided with a coaxial conical sealing surface 38 which provides the sealing when the valve is closed.

Rotatable valve member 48 is a screw-like member consisting of a larger diameter head 54 and a threaded body portion 50 engaging the internal threads on large diameter bore 36 on large diameter portion 42 of the stationary valve member. Threaded body portion 50 terminates at its lower end in a coaxial conical end to engage sealing face 38 of seat 46. Rotatable valve member 48 is provided with an axial bore 52 through the head 54 and much of the threaded body portion 50. Near the lower end of threaded portion 50, the axial bore 52 is terminated in a lateral bore 52a. Lateral bore 52a is directed out through the conical end of threaded body portion 50 to oppose the sealing surface 38 of seat 46. Accordingly, if rotatable valve member 48 is rotated until its conical end is brought into snug contact with the resilient seat 46, the bore 52-52a is sealed off from axial bore 34 and all flow through the valve is stopped.

The head portion 54 of the rotatable valve member 48 is provided with a cylindrical surface which may be grasped with the fingers and turned about the axis to open and close the valve. Bore 56 accepts, frictionally engages, and seals the leuer fitting 58a of a reagent tube 58 in a coaxial arrangement. Due to the frictional engagement between reagent tube 58 and rotatable valve member 48, any rotational movement of reagent tube 58 about the common axis operates the valve. Thus, if tube 58 is turned by the operator, the rotational movement raises or lowers rotatable valve member 48 into stationary seat 46. The spacing of the end of the lateral bore 52a from shoulder 38 of seat 46 controls the rate of passage of fluid through the valve means 30. The flow rate through each valve is similarly easily individually controlled by the operator by merely rotating the reagent tube above the valve.

Affixed to smallest diameter portion 41 of stationary valve member 32 is stainless steel tip 60 which directs the eluted fluid into a test tube 62 or other receptacle placed therebelow in the vacuum chamber. The steel tip is preferably a two diameter tubular piece, the larger diameter of which is selected to snugly engage the outer surface of small diameter valve portion 41. The smaller diameter portion of the steel tip 60 may be selected to be about the size of the bore through the valve or a little larger. When contact of the liquid sample with metal should be avoided, the steel tips 60 may be replaced with, for example, short lengths of Teflon ® tubing.

Figure 4:
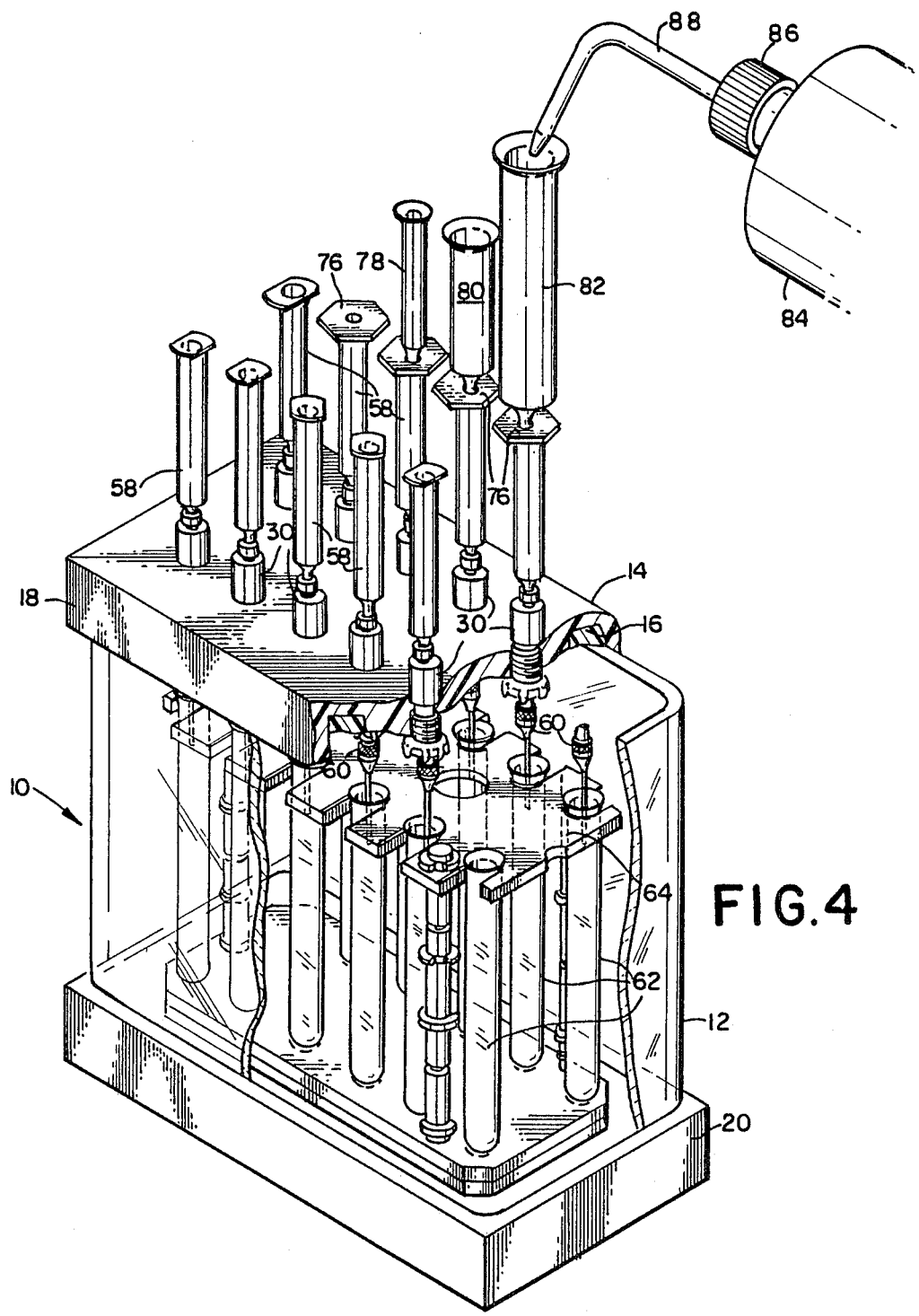
FIG. 4 is a perspective view of a vacuum manifold apparatus made in accordance with the invention partially broken away for visibility of the inner structure.
Figure 5:
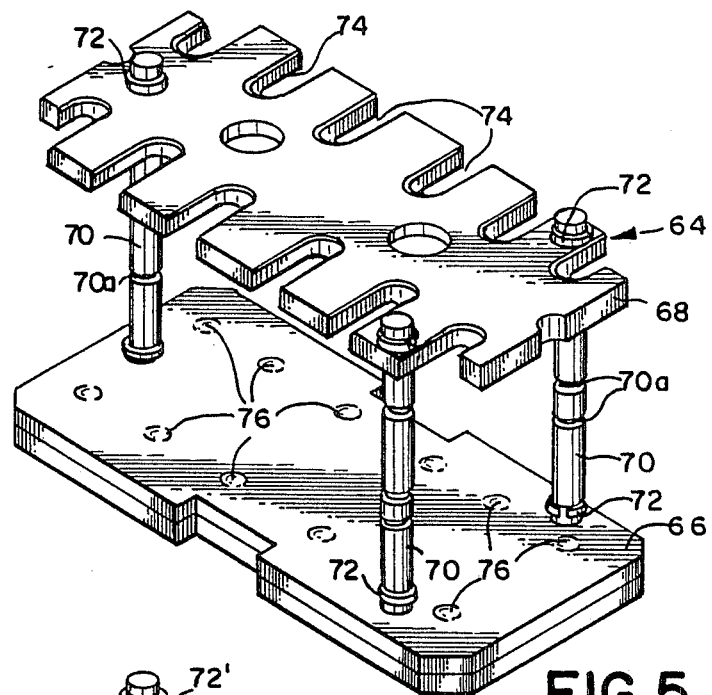
FIG. 5 is a perspective view of a collection rack for use with a vacuum manifold apparatus made in accordance with the invention set in a first position.
Figure 6:
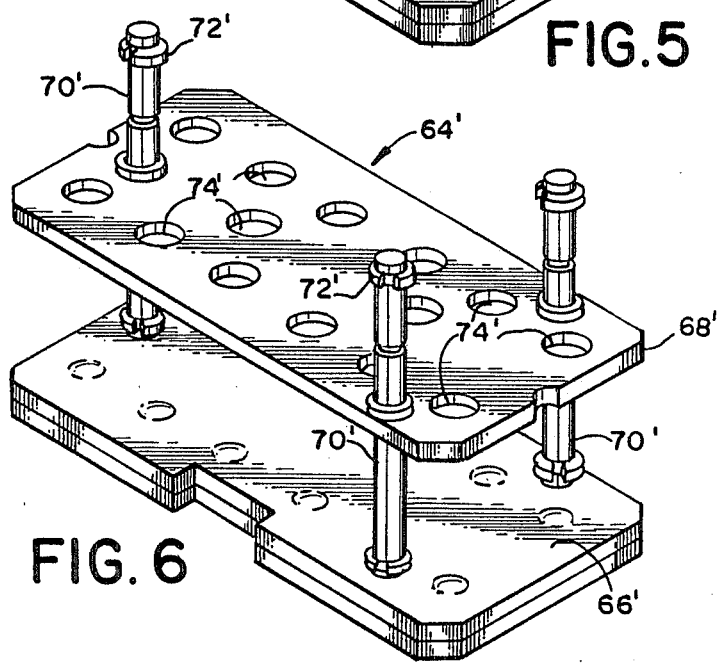
FIG. 6 is a perspective view of a collection rack shown differing somewhat from that of FIG. 5 set in a second position.

Referring to FIGS. 5 and 6, racks are shown which can accommodate test tubes and other types of receptacles for receiving and collecting the liquid samples discharged from tips 60 into the vacuum chamber. A preferred rack is shown having a base 66 to which is affixed a top holder 68 supported by columns 70. When the rack is positioned inside the vacuum chamber, base portion 66 rests on the bottom of vacuum chamber 12, as seen in FIG. 4. Columns 70 are held in place by snap rings 72 in cooperation with grooves 70a provided on the columns. The top holder 68 is provided with slots 74 on each side of the structure to receive and hold test tubes. On the base 66 are provided dimples 76 to provide stable support for the test tubes.

As shown in FIG. 6, holes 74', rather than slots, may be used to accommodate the test tubes. FIG. 6 also reveals that the top holder 68' may be placed in different preselected elevational positions on the columns 70'. Corresponding parts in FIGS. 5 and 6 are similarly numbered with the number designations in FIG. 6 being given as primes.

As shown in FIG. 1, it is possible to add additional reagent tubes to the reagent tubes 58 in a series flow path. An additional tube 78, 80, or 82 is added through the use of an intermediary closure 76, which provides a stopper closing the top of tube 58 and a receptacle to receive and frictionally engage the leuer fitting of second reagent tube 78, 80 or 82. In some processes and treatments, sequential processing of liquid samples is desirable, and may be achieved by the use of the coupled, successive reagent tubes as shown in FIGS. 1 and 4. As shown in FIG. 4, a reagent bottle 84 supplies reagent through the cap 86 having a spout 88 to direct fluid directly into the individual tubes.

In some instances, solid phase extraction involves a two step process. First, a solution which is to be analyzed and is believed to contain a certain constituent is fed through a reagent tube in which the solid reagent is capable of retaining the constituent. Often, different constituents are removed sequentially by different solid packings. A solvent is then eluted through the reagent tubes to release the retained constituent in the eluent. The many possible variations of solid phase extraction that can be performed with a device made in accordance with the invention, using different arrangements and combinations of reagent tubes, are too numerous to mention and the individual reagents and processes are not material. It would be obvious to those skilled in the art to perform any type of elution using the manifold of the present invention.

Figure 7:
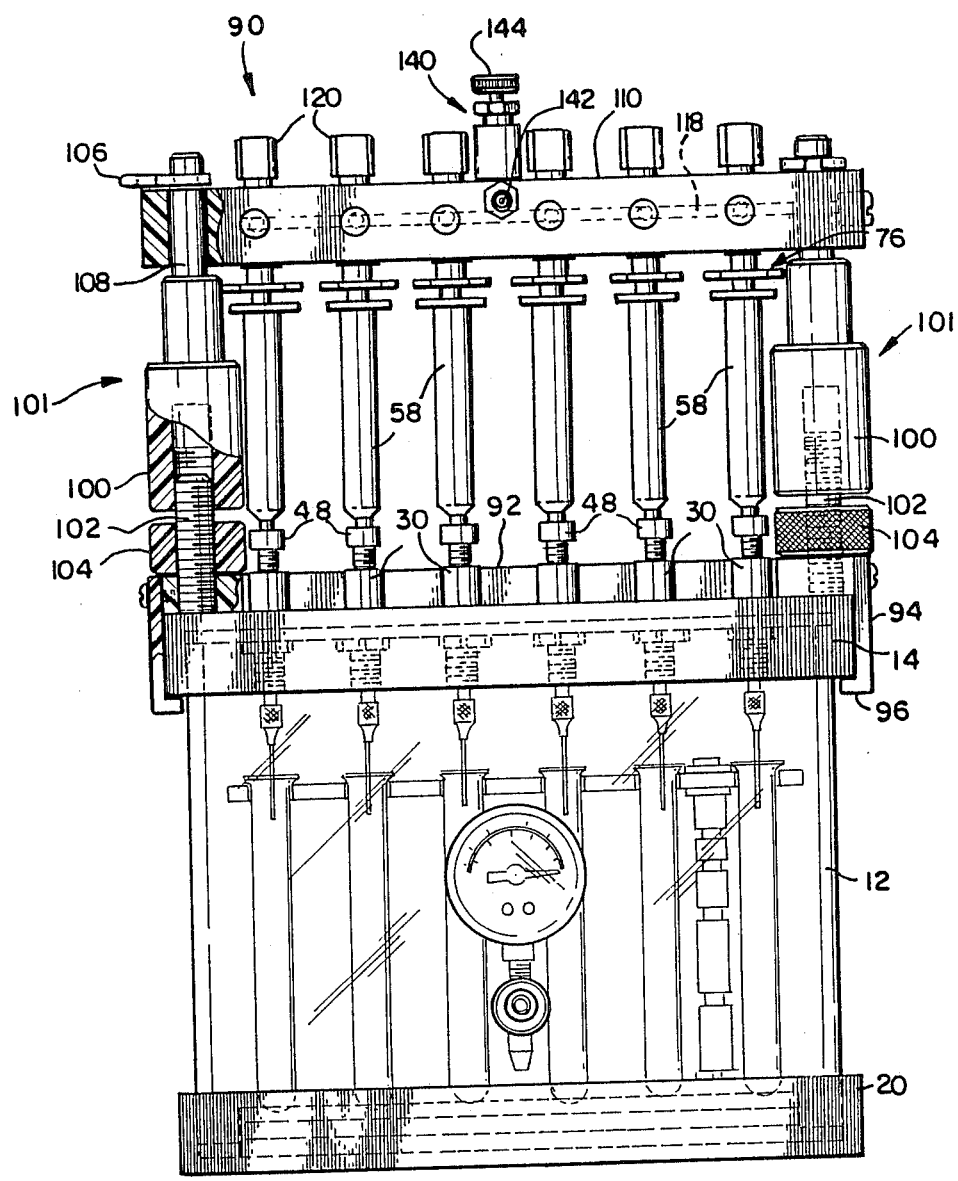
FIG. 7 is a front elevational view of a nitrogen purge device made in accordance with the invention affixed onto a vacuum manifold device made in accordance with the invention.

Referring now to FIG. 7, the vacuum manifold device and reagent tubes described hereinbefore are shown attached to a nitrogen purge attachment designated generally as 90. The nitrogen purge device provides a flow of nitrogen (or other gas) to the system. One purpose of the nitrogen purge device is to evaporate residual solvent contained in the test tubes within the vacuum chamber 12, thereby evaporating the eluent to dryness. Another object is to dry the solid material within reagent tubes 58 to remove solvent. In addition, the nitrogen purge can serve to drive liquid samples through the reagent tubes 58, increasing the rate of sample preparation.

Referring to FIG. 7, in the arrangement shown, a full set of reagent tubes 58 is shown attached to valves 30 of the vacuum manifold. As shown, the nitrogen purge assembly is supported above the tubes 58 and provided with individual couplings which fit into stoppers 76 in the tops of the reagent tubes.

The nitrogen purge attachment is preferably provided with means to mechanically support it from the cover 14 of the vacuum manifold. The attachment and support structure includes a base bar 92 which rests atop cover 14 of the vacuum manifold. As seen in phantom in FIGS. 7 and 8, base bar 92 extends the length of the cover 14 between the two rows of valves 30 into which reagent tubes 58 are fitted below the rotatable portion 48 of the valves 30. The width of base bar 92 is increased at its ends beyond the valves to increase stability. As seen in FIG. 7, clamp pieces 94 are bolted into the ends of the base bar which is essentially coterminous with cover 14. The clamp pieces 94 have flanges 96 which snugly embrace the bottom of the sidewalls of the manifold cover 14.

The nitrogen purge assembly further comprises a manifold plate 110, which is mounted parallel to the top of cover 14 above the reagent tubes 58. Manifold plate 110 is supported from the base bar by columns generally designated 101. Threaded into base plate 92 are threaded bolts 102 forming the bottom of columns 101 and protruding upwardly from base plate 92. Lock nuts 104 are threaded onto bolts 102. At the top of each column is a post 108. The manifold plate 110 is provided with bores to accommodate and hold posts 108 atop the shoulder of manifold plate 110. C-rings 106, which are removably engaged in grooves in posts 108 above the manifold, hold the posts 108 to manifold plate 110. Rotatably affixed to posts 108 are internally threaded coaxial adjustment cylinders 100 which engage the threaded bolts 102 and by their rotation permit height adjustment of the manifold above the cover 14, thereby permitting the manifold plate 110 to have its spacing from the top cover 14 of the manifold adjusted. The manifold plate 110 may be raised, lowered or removed by turning adjustment cylinders 100 in order to accommodate and connect to reagent tube 58.

Manifold plate 110 is provided with interconnected passages or bores connected with a nitrogen inlet valve 140 into the passages in plate 110 through valve 140. A nitrogen input coupling 142 is provided for attachment to a source of nitrogen (not shown). Nitrogen inlet valve 140 is a needle-type control valve whereby the flow of nitrogen is controlled by turning cap 144. When in the open position, needle valve ports 148 and 150 are interconnected to allow nitrogen to pass through the pattern of conduits shown in phantom in FIG. 8. The conduits are bored into top plate 110 from one edge, and have their open ends plugged as seen in FIG. 9. Nitrogen from inlet 140 passes into central conduit 118, and thereafter into parallel lateral conduits 118*a*, as shown in FIG. 8. Auxiliary conduits 118*a* supply nitrogen to valve control members 120. valve control members 120 pass through the manifold plate 110 as seen in FIG. 9. As shown in FIG. 9, each valve control member 120 receives nitrogen through conduit 118*a* intersecting the valve bore 126 at right angles. The valve control member 120 extends through the bore 126 in manifold plate 110 and is retained downwardly by a shoulder which acts as a stop upon inserting the member 120 and upwardly by a C-shaped snap ring 128 which is retained in a circumferential groove below the manifold plate 110. The valve control member does not have a valve function itself. However, due to its connection to a reagent tube 58, and rotation of the valve control member within the bore conveyed to the reagent tube 58, it can cut off the flow of nitrogen to the vacuum chamber by closing valve 30. Hourglass shaped piece 124 functions to assure that, whatever rotatable position valve control member 120 assumes, there is communication between conduit 118*a* and port 132. Port 132 extends out the bottom of the valve through fitting 130 to sealingly engage the opening in stopper 76 in the reagent tube 58. O-rings 122 within the bore 126 serve to maintain a gas-tight seal in the bore even though the top and bottom edges of hourglass portion 124 are designed to contact the bore. The construction permits axial insertion of the valve control members into the bore and operational movement thereof.

Referring to FIG. 9, nitrogen circulating in auxiliary conduits 118*a* will enter the entry port in each valve 120, and will proceed through valve 120 via conduit 132 into reagent tube 58. If nitrogen inlet valve 140 (FIG. 10) is in its open position, nitrogen will be supplied into each of the reagent tubes 58. The rate of flow of this nitrogen purge may, of course, be controlled by adjusting the nitrogen inlet valve 140.

It is noted that due to the frictional engagement between tip 130 of valve 120 and plug 76 on reagent tube 58, any rotational movement exerted on valve 120 is translated to the reagent tube 58. As noted earlier, each reagent tube 58 is frictionally engaged with rotatable valve member 48 of valves 30, and rotation of rotatable valve member 48 in one direction tends to open and in the other to close the valve 140 to permit or stop flow through valves 30 on the vacuum manifold. Accordingly, the flow of nitrogen into the vacuum chamber 12 by any given valve 30 may be regulated, or shut off entirely, by rotating valve 120 on manifold plate 110.

In an alternate application of the invention, using shorter columns, or none at all, valve control members 120 of manifold plate 110 may be fitted directly onto valves 30 of manifold cover 14. In this application, the reagent tubes 58 are omitted, of course. Tips 130 of valve control members 120 may be fitted directly into rotatable valve members 48 of valve 30. In this manner, nitrogen is fed directly from manifold plate 110 into valves 30, without passing through reagent tubes 58. This use of the nitrogen purge assembly would be useful, for example, when it is desired to evaporate the contents of test tubes inside the vacuum chamber without drying the reagent tubes 58.

The nitrogen purge assembly is preferably formed of hard plastic, such as polypropylene, with the exception of certain parts including the nitrogen inlet valve 140 and threaded bolts 102, which are preferably metal.

The foregoing discussion of the preferred embodiment and best mode of practicing the invention are intended as examples and not intended to limit the scope of the invention as set forth in the following claims. All modifications and various embodiments within the scope of the claims are intended to be within the scope of the invention.

We claim:

1. A vacuum manifold for use in simultaneous solid phase extraction of a plurality of liquid samples, comprising:
   a vacuum chamber having means defining an access opening;
   a removable cover for the access opening of said vacuum chamber which is capable of sealing vacuum tight thereto;
   means defining a plurality of generally parallel flow paths through said cover including a plurality of valve means for closing off and regulating flow of liquid samples through respective flow paths into said vacuum chamber, each of said plurality of valve means having a rotatable valve member which is rotatable about an axis generally parallel to the general direction of flow through each flow path such that rotation of each rotatable valve member permits flow adjustment and closing of each respective valve means; and
   means for attaching a vacuum source to said vacuum chamber to create a vacuum therein.

2. The vacuum manifold set forth in claim 1 wherein each rotatable valve member is provided with a coaxial bore fitting for receiving, frictionally engaging and coaxially supporting a reagent tube, wherein each coaxial bore fitting is extended by a conduit through each respective valve member, which conduit may be opened or closed whereby each valve means may be open or shut by axially rotating a reagent tube associated therewith.

3. The vacuum manifold set forth in claim 1 in which there is provided an auxiliary conduit network member providing gas conduits connected to a gas inlet and terminating in parallel output couplings positioned relative to one another for direct sealing engagement with means defining bores in respective rotatable valve members or with means defining bores in reagent tubes coaxially mounted into respective rotatable valve members.

4. The vacuum manifold set forth in claim 2 in which each valve means includes a stationary valve body fixed to the cover having means defining an axial bore through each body with a circumferential valve seat having at least a radial component and each rotatable valve member is engaged with each respective stationary valve body to move relative thereto by rotation and each rotatable valve member by such rotation may be brought into engagement with each respective valve seat so that the conduit extends through each respective rotatable valve member and terminates in means defining a port closed by contact with each respective valve seat.

5. The vacuum manifold set forth in claim 4 in which each valve seat is provided by a resilient sealing member supported on a shoulder of each respective stationary valve member, such that the resilient sealing member provides a conical surface that engages a similar conical surface on each respective rotatable valve member through which a conduit port emerges.

6. The vacuum manifold set forth in claim 1 including support means within said vacuum chamber for supporting sample collection tubes comprising a rack including at least a base and a parallel tube support means, the support means having means defining openings with container engaging bounding edges, columns supported on the base and supporting the tube support means in a plurality of selected positions at various spacings from the base and including interacting means providing stable support at different levels.

7. The vacuum manifold set forth in claim 6 in which the support means includes a base defining a bottom of the vacuum chamber essentially parallel to the removable cover when attached to the chamber positioning the rack in the vacuum chamber to locate containers supported in the rack beneath each flow path through each respective valve means.

8. The vacuum manifold set forth in claim 1 wherein said cover includes a seal of resilient material on the cover corresponding in shape and size to the chamber access opening and positioned for engaging the means defining the access opening when closing the opening.

9. The vacuum manifold set forth in claim 8 wherein the seal is retained in a channel in the cover into which the means defining the access opening fits.

10. The vacuum manifold set forth in claim 9 in which the cover has sidewalls conforming to and embracing the means defining the access opening of the chamber and the channel and seal are within, adjacent to and conforming to the shape of the sidewalls.

11. A vacuum manifold for use in simultaneous solid phase extraction of a plurality of liquid samples, comprising:
    a vacuum chamber having means defining an upwardly opening access opening;
    a removable cover for the access opening of said vacuum chamber which is capable of sealing vacuum tight thereto in a generally horizontal orientation;
    a plurality of valve means through said cover for admitting liquid samples into said vacuum chamber, each valve means having a stationary valve member having a means defining vertically oriented axial bore fixed to the cover and a rotatable valve member supported within each stationary valve member and rotatable about a generally vertical axis, each valve means being adjustable and closable by rotation of each respective rotatable valve member to control the rate of flow of liquid sample through each valve means; and
    means for attaching a vacuum source to said vacuum chamber to create a vacuum therein.

12. The vacuum manifold set forth in claim 11 wherein each stationary valve member includes a circumferential valve seat having a horizontal component, and a coaxial rotatable valve member in threaded engagement with each respective stationary valve member and closing the axial bore except for a conduit through each respective rotatable valve member which is closed by engagement of a surface through which the conduit emerges with each circumferential valve seat on each respective stationary valve member.

13. The vacuum manifold set forth in claim 12 wherein each coaxial rotatable valve member includes a sealing seat portion on a shoulder between two bore diameters within each respective stationary valve member and having at least a component transverse to the axis against which an end surface of each respective rotatable valve member engages and at which a conduit terminates, whereby, by rotation of each rotatable valve member, each rotatable valve member may be brought to bear against each respective seat portion to close each respective coaxial rotatable valve member.

14. The vacuum manifold set forth in claim 13 wherein each rotatable valve member is provided with a conical end face at which a conduit terminates and each sealing seat portion is provided by a resilient washer supported on a shoulder of each stationary valve member, wherein each resilient washer presents a generally conforming conical sealing surface to the conical end face of each rotatable valve member.

* * * * *